United States Patent
Tolvanen-Laakso et al.

(10) Patent No.: US 8,038,642 B2
(45) Date of Patent: Oct. 18, 2011

(54) SYSTEM FOR DELIVERING ANESTHESIA DRUGS TO A PATIENT

(75) Inventors: Heli Tolvanen-Laakso, Helsinki (FI); Leena Pesu, Helsinki (FI); Kimmo Uutela, Helsinki (FI); Börje Rantala, Helsinki (FI); Risto Rossi, Kauniainen (FI)

(73) Assignee: General Electric Company, Schenectady, NY (US)

( * ) Notice: Subject to any disclaimer, the term of this patent is extended or adjusted under 35 U.S.C. 154(b) by 797 days.

(21) Appl. No.: 11/551,289

(22) Filed: Oct. 20, 2006

(65) Prior Publication Data

US 2007/0149953 A1  Jun. 28, 2007

(30) Foreign Application Priority Data

Oct. 21, 2005 (EP) .................................... 05109830

(51) Int. Cl.
*A61N 1/30* (2006.01)

(52) U.S. Cl. ........................................... 604/19
(58) Field of Classification Search ............ 604/19
See application file for complete search history.

(56) References Cited

U.S. PATENT DOCUMENTS

| | | | |
|---|---|---|---|
| 6,631,291 B2 | 10/2003 | Viertio-Oja et al. | |
| 2001/0022182 A1 | 9/2001 | Heitmeier et al. | |
| 2002/0169636 A1 | 11/2002 | Eggers et al. | |
| 2003/0040700 A1* | 2/2003 | Hickle et al. | 604/67 |
| 2003/0051737 A1 | 3/2003 | Hickle et al. | |
| 2003/0171733 A1 | 9/2003 | Hoelscher | |

FOREIGN PATENT DOCUMENTS

| | | |
|---|---|---|
| DE | 198 29 018 A1 | 1/2000 |
| EP | 1 547 631 A1 | 6/2005 |
| WO | WO 98/10701 A | 3/1998 |
| WO | WO 02/32036 A2 | 4/2002 |
| WO | WO 2004/000400 A | 12/2003 |
| WO | WO 2004000400 A2 * | 12/2003 |

* cited by examiner

*Primary Examiner* — Nicholas D Lucchesi
*Assistant Examiner* — Diva Ranade
(74) *Attorney, Agent, or Firm* — Global Patent Operatin; Jonathan E. Thomas

(57) ABSTRACT

The invention relates to a system for delivering anesthesia drugs to a patient. The system comprises means for feeding anesthesia drugs to the patient treated, a measuring device for measuring at least one parameter relating to the effects of the anesthetic drugs fed to the patient, a patient monitor to show the results measured by the measuring devices, and feeding means for feeding patient demographics to the system. The system further comprises means for visual planning of the anesthesia drug delivery before the drugs are actually fed. The system can also comprise means for anesthesia management for drug interaction during the treatment.

13 Claims, 4 Drawing Sheets

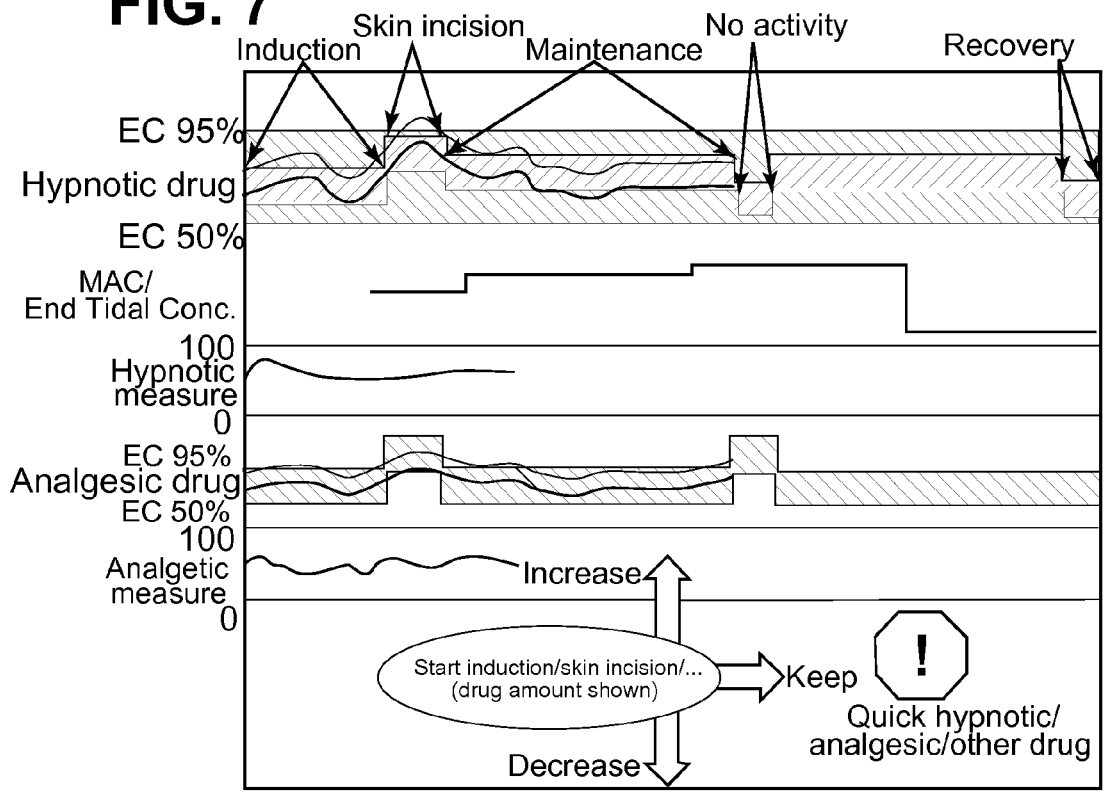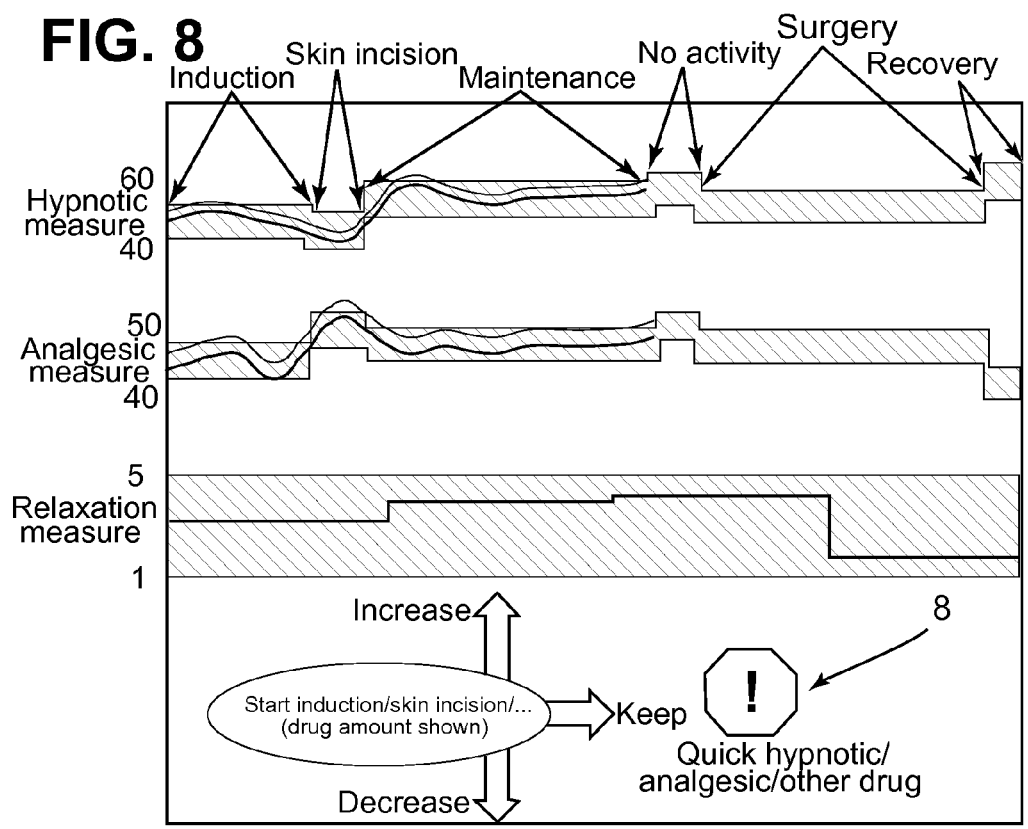

SYSTEM FOR DELIVERING ANESTHESIA DRUGS TO A PATIENT

BACKGROUND OF THE INVENTION

1. Field of the Invention

The invention relates to a system for delivering anesthesia drugs to a patient, the system comprising means for feeding anesthesia drugs to the patient treated, a measuring device for measuring at least one parameter relating to the effects of the anesthetic drugs fed to the patient, a patient monitor to show the results measured by the measuring devices, and feeding means for feeding patient demographics to the system.

2. Discussion of Related Art

Anesthesia is typically given (approximately 90% of the normal day surgery) by both intravenous and inhalational gas anesthetics. There exists however certain amount of users that practice total intravenous anesthesia (TIVA) especially in Europe and more widely TIVA can be used in small & fast cases. During the anesthesia anesthesiolgist titrates the anesthetics based on drug models and the drug distribution over time as well as by following the physiological parameters (the effect or responses to the drug given).

Intravenous (IV) drug distribution and model behaviour can be followed sometimes from an intravenous pump (IV pump) display (there exists some devices on the market, called TCI pumps) but in most of the cases there is no modelling or distribution shown. In practise the anesthesiologist still calculates an appropriate amount of drug for the particular patient with a calculator or in his head (the inputs being weight and height). This happens with the commonly used syringe pumps having no models inside them. Also the pumps are many times away from the parameter display (patient monitor) and so the effects and responses to the drugs are shown separately from the IV drug management.

The gas anesthetic statistical model called MAC (minimal alveolar concentration) is shown in most anesthesia monitors. This is however a quite approximative measure, since its background is on tests where the endpoint has been skin incision (and not for example the true hypnosis level). This measure is shown in some integrated anesthesia machines in the parameter display (patient monitor), so the anesthesiologist can see the drug effect and response quite easily. Another measure of gas anesthetics effect is the end tidal agent (ET) or fraction of inspired agent (FI), which can be shown in anesthesia monitor.

The first step to integrate the IV drug models into one display has been taken by GE Healthcare by launching a Care Assistant Suite (CAS) in European Anesthesiologist Congress 2005. This display shows IV drug models and their synergetic effects in one display, which is mounted next to the patient monitor and the anesthesia machine.

During the years several systems and methods have been developed in order to facilitate anesthesia drug deliveries. As typical examples of the solutions of the prior art the following publications can be mentioned.

PCT Publication WO0232036A2 describes a method and an apparatus for monitoring anesthesia drug dosages, concentration, and effects using N-dimensional representations of critical functions. This patent describes a method, system and apparatus for the monitoring, diagnosis and evaluation of the state of a dynamic system. The method and system provides the processing means for receiving sensed and/or simulated data, converting such data into a displayable object format and displaying such objects in a manner such that the interrelationships between the respective variables can be correlated and identified by a user. In particular, this invention is directed to the processing and display of drug data for the use of doctors in the process of monitoring or administering drugs to patients.

U.S. patent application 2003/0051737 A1 describes an apparatus and a method for titrating drug delivery. In this application a method and apparatus for reducing the workload of titrating drug (sedative, amnesic and & or analgesic) to effect while leaving clinician users in control of a related procedure is described. A drug delivery device is controlled to achieve a target drug concentration at a selected site in the patient or a predetermined infusion rate waveform. The time profile of the target drug concentration or a predetermined infusion rate waveform is controlled by a drug state model that uses clinical heuristics to implement safe, pre-defined changes in the target drug concentration or infusion rate and user-commanded changes in target drug concentration or infusion rate.

U.S. patent application 2002/0169636 A1 describes a system and method method for managing patient care. The application is directed to a system and method for providing care to a patient, comprising a patient care device having a number of configuration databases stored in a memory of the device. Each configuration database preferably includes protocols, operating limits, rule sets and/or operating features that collectively define an operating environment, or personality, of the device. The selected protocol includes default parameters for delivering the drug, and the label optionally includes instructions for deviating from the default protocol.

U.S. Pat. No. 6,631,291 describes a closed loop drug administration method and apparatus using EEG complexity for control purposes. A closed loop method and apparatus for controlling the administration of a hypnotic drug to a patient. At least one measure of the complexity of the EEG signal data is derived from the patient. An EEG signal complexity measure obtained from the cerebral activity of the patient can be advantageously used in conjunction with a measure of patient electromyographic (EMG) activity to improve the response time of hypnotic level determination and of the feedback control of drug administration. A pharmacological transfer function may be used, along with pharmacokinetic and pharmacodynamic models.

EP Patent Application 1 547 631 A1 describes a computer-controlled intravenous drug delivery system. The system described relates to controlling and steering intravenous anesthesia (IVA) and/or the application of other intravenous drugs to a patient in a safe and user friendly way. Less experienced anesthetists profit from expert knowledge stored, retrievable and usable via the system.

The systems and methods known in the prior art are however rather complicate and not so user friendly and flexible in every day life.

BRIEF DESCRIPTION OF THE INVENTION

The object of the invention is to obtain a system with which the disadvantages of the prior art can be eliminated. This is obtained with the invention. The invention is an enhanced way to do anesthesia. The invention is related especially, but not exclusively to balanced anesthesia containing intravenous and inhalational gas anesthetics. The basic idea of the system described could be referred for example to the aviation pilots working place. The user could do the anesthesia planning and management in a display that would be straight in the care area and next to the patient monitor and anesthesia machine. This display could be the already mentioned third display (CAS) or it could be integrated into patient monitor and/or to the anesthesia machine. The invention is characterized in that the system comprises means for visual planning of the anesthesia drug delivery before the drugs are actually fed.

The advantage of the invention is its simplicity and flexibility. In other words the invention can be easily used with the known systems, for example the CAS display as described above. The invention can also be used in connection with patient monitors or anesthesia machines if needed. In other words the invention can be advantageously adapted to the various devices already existing for example in a hospital, and therefore investment costs are relatively low.

BRIEF DESCRIPTION OF THE DRAWINGS

In the following the invention will be described in greater detail by means of examples described in the attached drawing, in which FIG. 7 shows one possible embodiment of the user interfaces for the embodiment shown in FIG. 2, and FIG. 8 shows another possible embodiment of the user interfaces for the embodiment shown in FIG. 2.

DETAILED DESCRIPTION OF THE INVENTION

Figure 1:
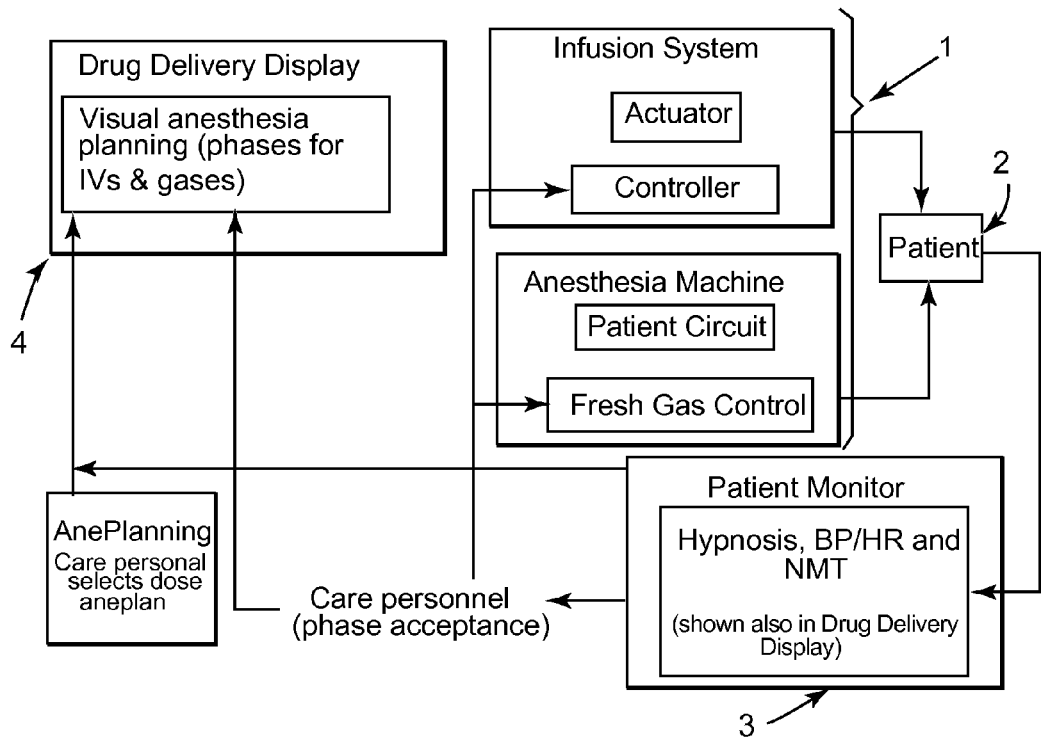
FIG. 1 shows a block diagram of the first embodiment of the invention.
Figure 2:
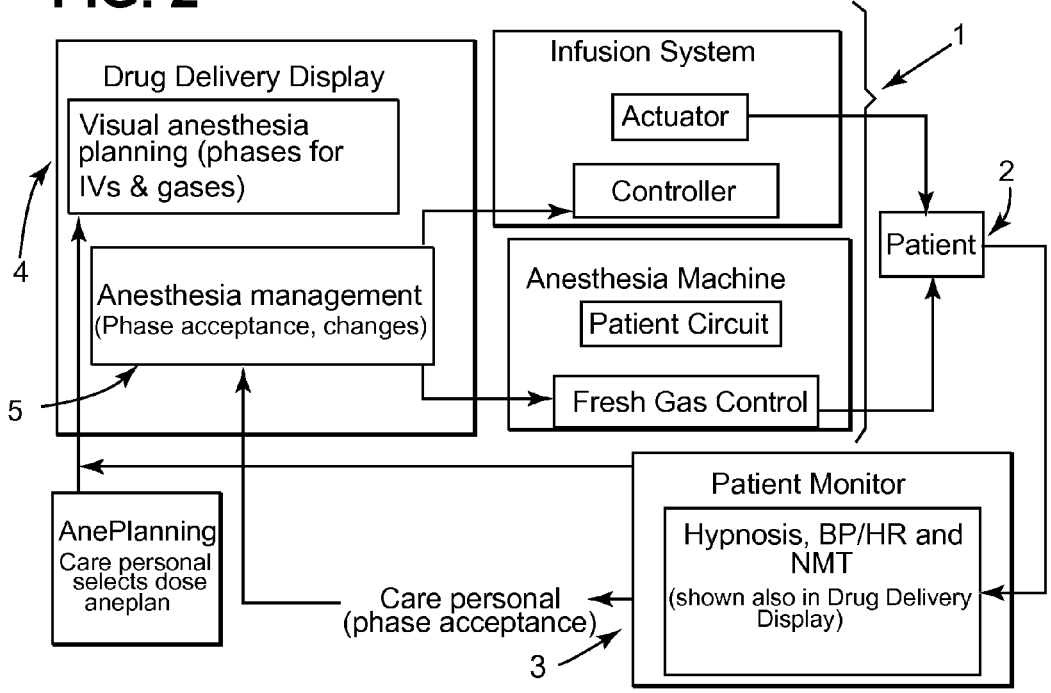
FIG. 2 shows a block diagram of the second embodiment of the invention.

The invention comprises two basic parts or components, namely anesthesia planning and anesthesia management. Both components are not always needed but anesthesia planning can be used also alone, i.e. without anesthesia management as shown in FIG. 1. FIG. 2 shows an embodiment of the invention in which both components are used.

The anesthesia planning would be done just before the case start by adjusting available templates or totally manually. It would include visually shown different phases (for example: induction, intubation, incision, maintenance, recovery). The templates would be done according the clinic experts and following clinics practices to use drugs and their interactions in different case types. The templates can be retrieved for example from an information management system. The patient demographics could be retrieved from the information management system or they could be inserted manually. The information management system could provide also possible drug related inconsistencies such as allergies. This information can also be fed manually into the system if needed.

The other component, namely anesthesia management would be done during the case when the actual drug delivery is happening. Then the effects of the drugs could be seen in the same display and the user could change the drug delivery based on the parameter information and the surgery changes. The embodiment using anesthesia management is shown in FIG. 2 as told above. The phase timing information would also come from the user by acceptance of the next phase. This way the next phase drug delivery would happen only after the previous phase is over.

The user interface of the anesthesia planning and management can be based on modelled drug effects PK (pharmacokinetic) and/or PD (pharmacodynamic) for IVs and MAC or ET or FI for gas anesthetics. Otherwise it can be based on parameters like hypnotic measure, analgetic measure and NMT (neuromuscular transmission) measure. This could be connected to a control algorithm that links the parameter values to the drug delivery changes.

The display could as well bring advisories and alarms based on the measured patient values or other clinical practices that would need to be taken into account during the case. There could be user set alarm limits and other safety features, for example quick hypnotic.

The anesthesia planning could be based on modelled drug effects PK and/or PD for IVs and MAC or ET or FI for gas anesthetics, and the parameter information could be shown aside. Otherwise it can be based on parameters like hypnotic measure, analgetic measure and NMT measure. The User Interface could be used also so that the parameter values would have user set limits and there would come advisories or alarms when the limits are approaching, so that the user could himself manage the drug deliveries. This is the case in the embodiment shown in FIG. 1, where there are not anesthesia management capabilities in the same display. The phase timing information could also come from the user by acceptance of the phases.

As told above the invention is related to anesthesia control especially in balanced anesthesia containing intravenous (IV) and inhalational gas anesthetics. It should however be noted that the invention can also quite well be used in connection with intravenous anesthetics only or respectively with inhalational anesthetics only. The invention combines visual anesthesia planning done before the case with the anesthesia management during the anesthesia. The system brings to the user an easier way to manage different anesthesia phases by giving a user interface where both the IVs and gas anesthetics can be managed from the same display. The anesthesia planning gives the possibility for the clinic to spread the best practices by using the predefined anesthesia templates for different anesthesia cases. The phases can be visualized for example on the basis of drug modelling for intravenous anesthetics, gas anesthetics or end tidal concentration.

The system of the invention comprises means 1 for feeding anesthesia drugs to the patient treated. The means 1 for feeding anesthesia drugs can comprise infusion system or/and anesthesia machine. The system comprises further measuring devices 2 for measuring parameters relating to the effects of the anesthetic drugs fed to the patient, and a patient monitor 3 to show the results measured by the measuring devices. The system comprises also feeding means for feeding patient demographics to the system. Said means can comprise appropriate equipment for manual feeding or/and said means can be connected to an information management system available. The information management system can be adapted also to feed all kinds of other important information to the system, for example eventual drug related inconsistencies such as allergies, diseases, previous drug delivery related problems etc. The essential idea of the invention is that the system further comprises means 4 for visual planning of the anesthesia drug delivery before the drugs are actually fed. The invention can also comprise means 5 for anesthesia management for drug interaction during the treatment. The means 5 can be seen in FIG. 2, which shows the embodiment of the invention using both components of the invention.

Referring again to FIG. 1 it is important to see that in this embodiment only one component, namely the anesthesia planning and also phase acceptance would be possible. Some advisories and/or alarms could come from the patient monitor 3 interface that is connected to the drug delivery display.

In the embodiment shown in FIG. 2 anesthesia planning and anesthesia management and also phase acceptance are possible. The system requires algorithm that links the parameter values, i.e. values obtained as a result from measurements from the patient, to the drug delivery changes. The anesthesia management system allows also the user to change the drug delivery according to the parameter information and surgery changes. The phase timing information can also here come from the user by acceptance of the next phase by using an appropriate mechanism for example through a touch screen, mouse or remote controller.

Figure 3:
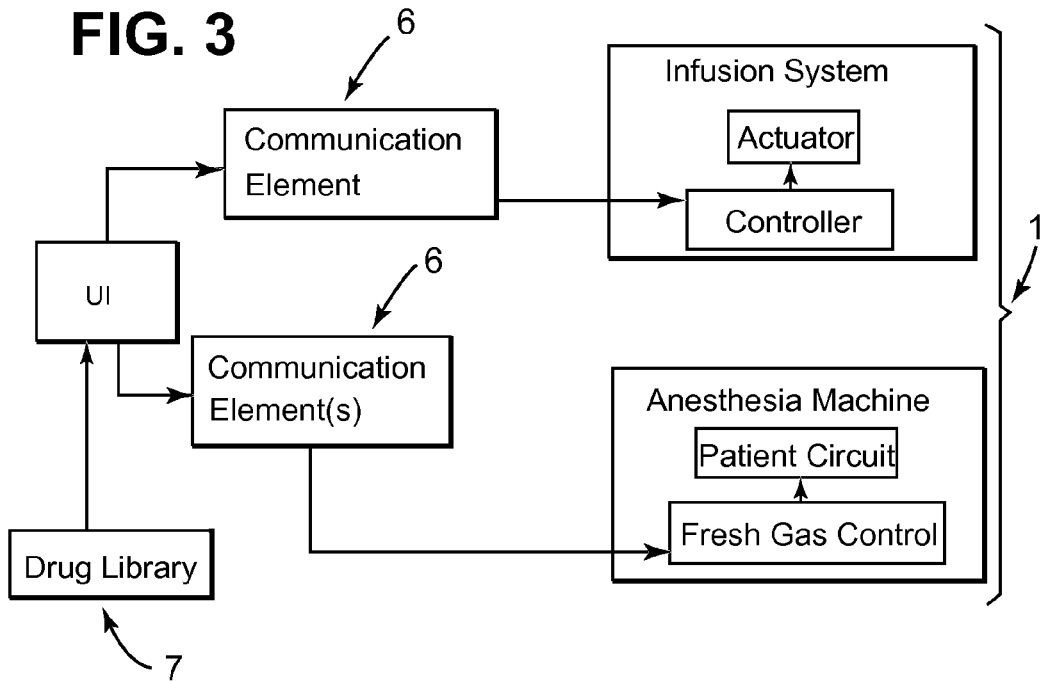
FIG. 3 shows a block diagram of one possible example of the communication systems for the second embodiment shown in FIG. 2.
Figure 4:
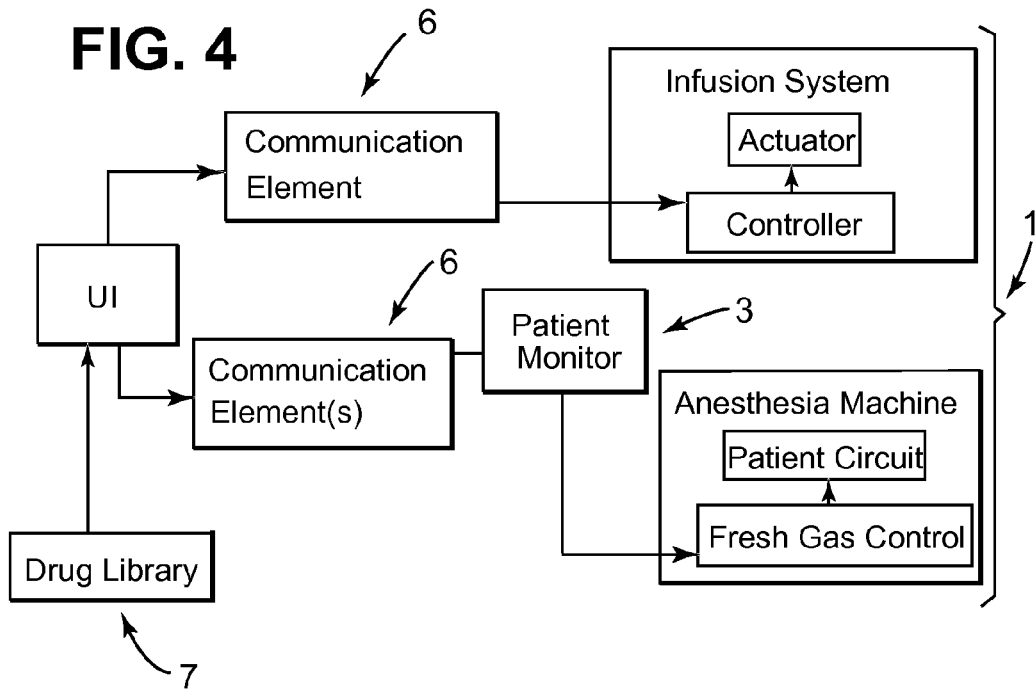
FIG. 4 shows a block diagram of another possible example of the communication systems for the second embodiment shown in FIG. 2.

As described above if the invention is seen on the upper level the different elements of the invention are those shown in FIGS. 1 and 2. FIGS. 1 and 2 show clearly that on this level the main elements in the system are means 1 for feeding anesthesia drugs, i.e. the infusion system and/or anesthesia machine, the user interface, i.e. means 4 for visual planning of the anesthesia drug delivery and means 5 for anesthesia management and communication elements 6 with which the user interface can communicate with for example means 4 and 5. Some embodiments of said communication elements are described more clearly in FIGS. 3 and 4. In the diagrams of FIGS. 3 and 4 block UI refers to the user interface comprising for example means 4 in FIG. 1 and means 4 and 5 shown in FIG. 2.

As shown in FIG. 3 the communication elements could be constructed from a software including drivers of the devices, networked server or similar. The communication elements could be part of the UI device as well. The UI device shall include watchdog or equivalent as a safety feature. The infusion system could be either a syringe pump or a TCI pump when the drug library 7 could be in the pump instead of a separate server. In the IV pump there would be the controller and actuator to handle the drug titration. The anesthesia machine would contain the fresh gas control unit (to do the actual drug titration) and the patient circuit to deliver the drugs to the patient. The patient monitor would provide the parameter information to the user s and to the Drug Delivery Display. The anesthesia machine would be left out in TIVA cases.

Another possibility is that the UI communicates with the anesthesia machine 3 through the patient monitor 3. This embodiment is shown in FIG. 4.

Figure 5:
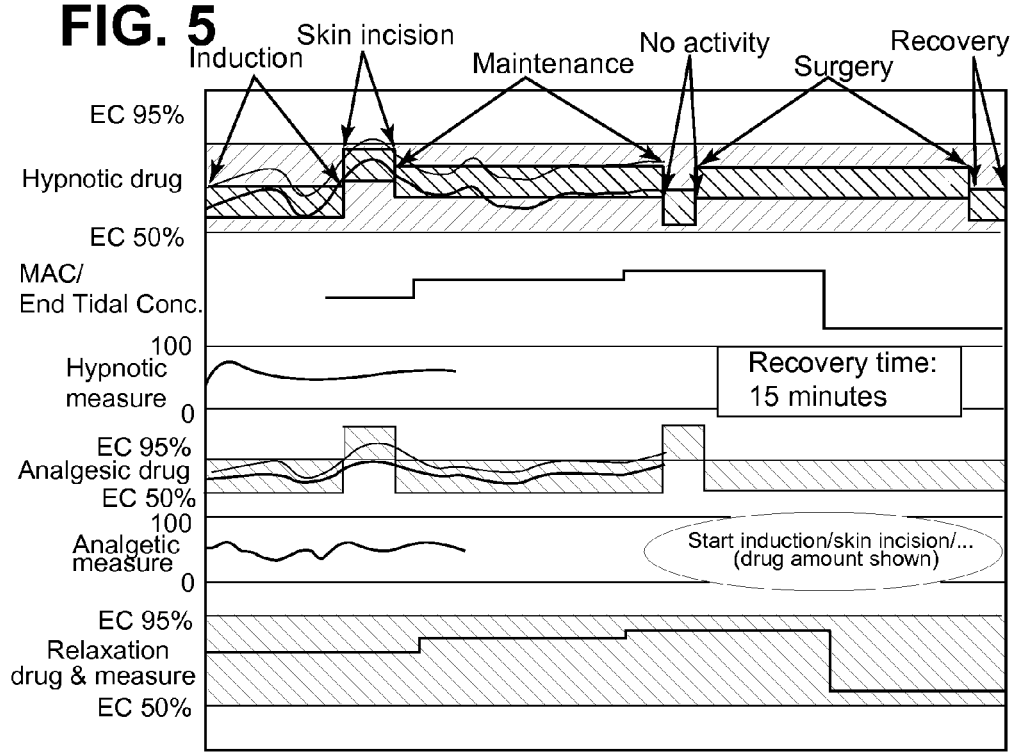
FIG. 5 shows one possible example of the user interfaces for the embodiment shown in FIG. 1.
Figure 6:
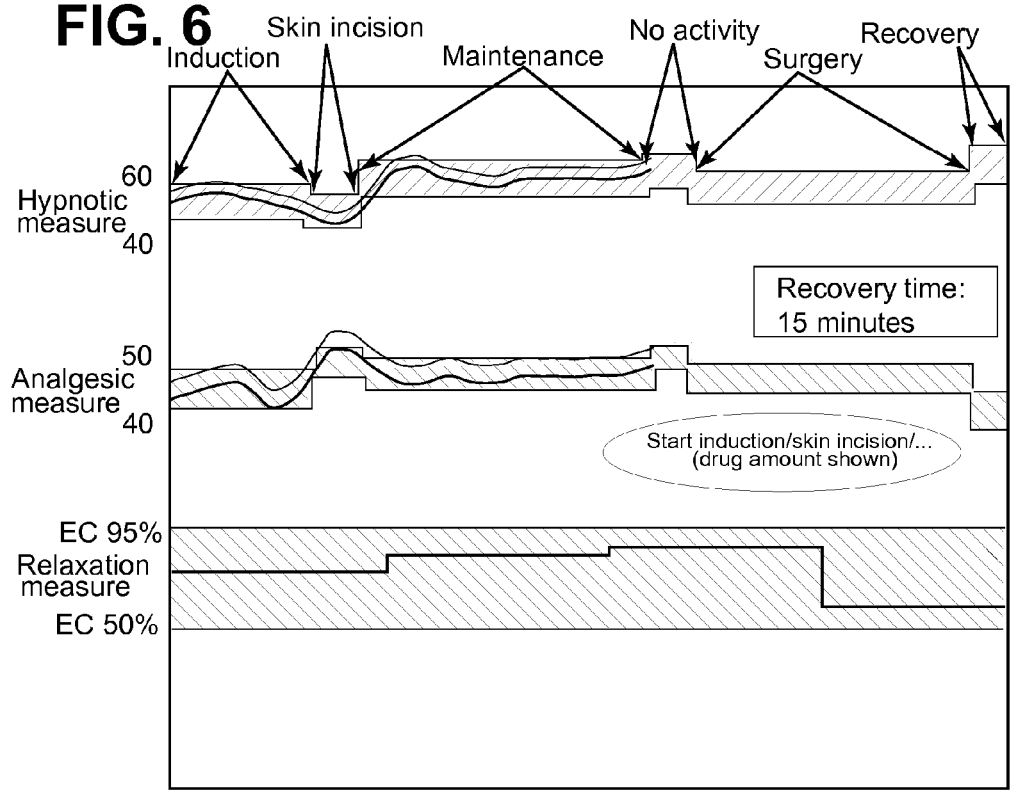
FIG. 6 shows another possible embodiment of the user interfaces for the embodiment shown in FIG. 1.

The user interface of the anesthesia planning 4 can be based on modelled drug effects PK and/or PD for IVs and MAC or ET or FI for gas anesthetics, and the parameter information could be shown aside as shown in FIG. 5. The parameters can for example be shown in the same display unit that is used for visual planning of the anesthesia drug delivery and for the anesthesia management. Otherwise it can be based on parameters like hypnotic measure, analgetic measure and NMT measure as shown in FIG. 6. Entropy and bi-spectral analysis of an EEG can be used as parameters representing the depth of hypnosis and unconsciousness during anesthesia. BP (blood pressure), HR (heart rate) and plethysmography can be used as parameters as well. The phases of the planning and management can also be based on the actual physiological parameter information. The User Interface shown in FIG. 6 could be used also so that the parameter values would have user set limits and there would come advisories or alarms when the limits are approaching, so that the user could by himself manage the drug deliveries.

The user interface of the anesthesia planning 4 and management 5 can be based on modelled drug effects PK and/or PD for IVs and MAC or ET or FI for gas anesthetics as shown in FIG. 7. Otherwise it can be based on parameters like hypnotic measure, analgesic measure and NMT measure as shown in FIG. 8. This could be connected to a control algorithm that links the parameter values to the drug delivery changes.

The display could as well bring advisories and alarms based on the measured patient values or other clinical practices that would need to be taken into account during the case. There could be user set alarm limits and other safety features 8, for example quick hypnotic.

The embodiments described above are by no means intended to restrict the invention, but the invention may be modified completely freely within the scope of the claims. Thus it is obvious that the details need not be exactly identical with those shown in the figures and described in the text, but other solutions are also possible within the spirit of the invention.

What is claimed is:

1. A system for delivering anesthesia drugs to a patient, the system comprising:
    means for delivering gas and intravenous anesthetics to the patient;
    a measuring device for measuring at least one parameter relating to the effects of the anesthetics on the patient;
    a patient monitor to show the results measured by the measuring device;
    feeding means for feeding patient demographics to the system; and
    means for visual planning of the anesthetics delivery comprising a user interface for displaying different phases of the anesthetics delivery action before the anesthetics are actually delivered to the patient.

2. The system of claim 1, further comprising means for managing interaction of the anesthetics during treatment of the patient.

3. The system of claim 2, wherein the means for visual planning of the anesthetics delivery and the means for managing interaction are displayed on a single display unit.

4. The system of claim 1, wherein the means for delivering gas and intravenous anesthetics delivers both gas and intravenous anesthetics to the patient.

5. The system of claim 1 wherein the phases are visualized on the basis of drug modeling for intravenous anesthetics, and minimum alveolar concentration (MAC), end tidal agent (ET), or fraction inspired agent (FI) for gas anesthetics.

6. The system of claim 1, wherein the phases are based on actual physiological parameter information.

7. The system of claim 1, wherein the means for visual planning of the anesthetics delivery retrieves templates from an information management system, and wherein each template is based on one or more of the knowledge of clinic experts, clinical practices, and the use of anesthetic and their interactions in different case types.

8. The system of claim 1, wherein timing of the phases is carried out by acceptance of the next phase.

9. The system of claim 2, wherein the means for managing interaction of the anesthetics is connected to a control algorithm that links the parameters to changes in the anesthetics delivery.

10. The system of claim 3, wherein the parameters measured from the patient are shown on the single display unit.

11. The system of claim 10, wherein the parameters are at least hypnosis measure.

12. The system of claim 3, wherein the single display unit shows advisories and/or alarms based on one or more of the parameters from the patient, clinical practices, and settled limits.

13. A system for delivering anesthesia drugs to a patient comprising:

at least one of an anesthesia machine and an infusion system for delivering anesthetics to the patient;

a measuring device for measuring at least one parameter relating to the effects of the anesthetics on the patient;

a patient monitor to show the results measured by the measuring device;

an information management system for feeding information including patient demographics to the system; and an anesthesia planning component for visual planning of the anesthetics delivery before the anesthetics are actually delivered to the patient, the anesthesia planning component comprising a user interface for displaying different phases of the anesthetics delivery action before the delivery of the anesthetics drugs to the patient.

* * * * *